United States Patent
Arumugam et al.

(10) Patent No.: US 11,975,011 B2
(45) Date of Patent: May 7, 2024

(54) MATRIX MESALAMINE EXTENDED RELEASE MINITABLETS AND ITS PROCESS THEREOF

(71) Applicant: ATOZ PHARMACEUTICALS PVT LTD, Chennai (IN)

(72) Inventors: Olaganathan Arumugam, Chennai (IN); Natarajan Venkatachalam, Chennai (IN); Arjun Arumugam, Chennai (IN)

(73) Assignee: ATOZ PHARMACEUTICALS PVT LTD, Chennai (IN)

( * ) Notice: Subject to any disclaimer, the term of this patent is extended or adjusted under 35 U.S.C. 154(b) by 0 days.

(21) Appl. No.: 17/517,353

(22) Filed: Nov. 2, 2021

(65) Prior Publication Data

US 2022/0133750 A1    May 5, 2022

(30) Foreign Application Priority Data

Nov. 3, 2020 (IN) .............................. 202041047916

(51) Int. Cl.
| | | |
|---|---|---|
| *A61K 9/20* | (2006.01) | |
| *A61K 9/00* | (2006.01) | |
| *A61K 9/48* | (2006.01) | |
| *A61K 31/606* | (2006.01) | |

(52) U.S. Cl.
CPC .......... *A61K 31/606* (2013.01); *A61K 9/0053* (2013.01); *A61K 9/009* (2013.01); *A61K 9/4808* (2013.01)

(58) Field of Classification Search
None
See application file for complete search history.

(56) References Cited

U.S. PATENT DOCUMENTS

| 10,071,058 B2 * | 9/2018 | Bowe | A61K 9/4808 |
| 2018/0000894 A1 * | 1/2018 | Malhotra | A61K 38/19 |

FOREIGN PATENT DOCUMENTS

WO    WO-2017125856 A1 *  7/2017

* cited by examiner

*Primary Examiner* — Susan T Tran

(57) ABSTRACT

Compositions for development of matrix type extended release mesalamine minitablets without use of any modified release coating, comprising a) mesalamine or its prodrug or derivatives thereof having a weight percentage in a range of 65-85 weight percentage with respect to the composition; b) at least one intragranular excipient having a weight percentage in a range of 3.5-22.5 weight percentage with respect to the composition; c) at least one binder having a weight percentage in a range of 2-6.5 weight percent with respect to the composition; and d) at least one extra granular excipient having a weight percentage in a range of 2-5 weight percentage with respect to the composition such that largest dimension in the minitablet is range of 1.00 mm to 2.8 mm. In another aspect of the present disclosure provides for a process of preparation of composition.

11 Claims, No Drawings

MATRIX MESALAMINE EXTENDED RELEASE MINITABLETS AND ITS PROCESS THEREOF

FIELD OF THE INVENTION

The present disclosure broadly relates to the field of pharmaceutical compositions, and particularly relates to the composition for development of matrix type mesalamine extended release minitablets and its process of preparing the same.

BACKGROUND OF THE INVENTION

Mesalamine is a drug, used in different dosage form, indicated for the various stages of inflammatory bowel disease or ulcerative colitis. Mesalamine products are available for different routes of administration, in different strengths, in different dosage forms and with different release mechanisms. List of currently available oral products are listed in the table below.

TABLE 1

| Active Ingredient | Dosage Form | Strength |
|---|---|---|
| Mesalamine | Capsule, Delayed Release and extended release | 400 mg |
| Mesalamine | Capsule, extended release | 375 mg |
| Mesalamine | Capsule, extended release | 250 mg & 500 mg |
| Mesalamine | Tablet, delayed release | 800 mg |
| Mesalamine | Tablet, delayed release | 1.2 gm |

Among those, only two products were manufactured as extended release in capsule dosage forms (with label claims of 250 mg, 375 mg and 500 mg). Of which, the capsules of 250 and 500 mg strength are dose proportionate, sprinkle formulations with truly extended-release characteristic, encapsulated with beads of desired (controlled) release of mesalamine (The 375 mg strength product was claimed to be delayed cum extended-release characteristic).

The controlled release capsule (250 and 500 mg) formulation is designed in such a way that capsules may be swallowed whole, or alternatively, the capsule may be opened, and the entire contents sprinkled onto applesauce or yogurt. The capsule contents/beads are prepared by layering mesalamine on sugar spheres, followed by either coating/microencapsulation with ethyl cellulose or ethyl cellulose with pore formers like hydroxypropyl methyl cellulose as release controlling agent. However, the method of preparation, process for manufacture of above controlled release beads involves multiple parameters, multiple steps, involving organic solvents and found to be expensive.

The recommended dosage for controlled release capsule (250 and 500 mg) is 1 g (4×250 mg capsules or 2×500 mg capsules), 4 times a day to the total daily dosage of 4 g. Each 250 mg and 500 mg capsule contains an approximate fill weight 545 and 800 mg respectively inside the capsule accounts for 45% and 62.5% drug load to the total weight of sprinkle formulation.

U.S. Pat. No. 9,402,815 describes a high drug load and ease of manufacture of mesalamine without spheronization, but by reservoir type dosage form by coating the core with controlled release polymer ethyl cellulose. Here the granulates of mesalamine without any additional aid or excipient were prepared using povidone as binder, thereby enables a high load of drug. Further, the granulates are sized and segregated with the size of interest and coated with ethyl cellulose as controlled release layer.

U.S. Pat. No. 9,114,083 describes the role of physical characteristics of granules, such as size, roughness, morphology and porosity and its importance in coating and thereby the release of the drug. It also describes how the aspect ratio plays a role in uniform coating. To get a sharper dissolution profile, the granules aspect ratio of said length to said cross-sectional dimension of greater than 0.7 and less than 2.2 are to be selected and critical for the development of batches at larger scales.

U.S. Pat. No. 8,501,226 also describes the method for coating mesalamine granules/pellets (reservoir type) to get the desired release profile with a coating mixture comprising two polymers of which one is water soluble. The patent further claims the tuning of water soluble polymer to obtain coated granules with desired controlled release profile.

U.S. Pat. No. 5,310,558A patent describes the preparation or process of programmed release dosage form as outer covering made of hydrophobic layer or combination of hydrophobic and hydrophilic/surfactant layer on core (reservoir type) made of active ingredient mesalamine.

U.S. Pat. No. 6,773,720B1 patent describes the controlled release oral pharmaceutical compositions of 5-amino salicylic acid in which the mesalamine is inglobated partially in molten lipophilic matrices by kneading, extrusion and or granulation subsequently the lipophilic matrices are dispersed into hydrophilic matrices. Then the granules are mixed with other excipients for tableting or compression.

In sprinkle formulations i.e. "labeled for sprinkle", size of beads is critical to administer with soft foods and it's swallowed without chewing to maintain the integrity of coating layers and thereby the release mechanisms. Meeting the goals of high drug load, controlled release in matrix minitablets without spheronization or functional encapsulation/coating technique (i.e. coating or layering with enteric or controlled release polymers) is challenging.

To overcome the above drawbacks the present disclosure discloses a composition and its process to entail ease of manufacturing of controlled release matrix minitablets of mesalamine, which doesn't involve (a) spheronization process (b) multicomponent layering process (e.g. layering non pareils with drug and controlled release polymer etc. (c) melting of lipophilic or hydrophobic waxy excipients, (d) enteric/controlled/sustained release polymeric coating process or (f) multiple steps involving one or more process described above. Most importantly matrix type minitablets of controlled release characteristic free of nonpareil seeds or functional coating layers.

The above information is presented as background information only to help the reader to understand the present disclosure. Applicants have made no determination and make no assertion as to whether any of the above might be applicable as prior art with regard to the present application.

OBJECT OF THE INVENTION

The principal object of the present disclosure is to provide a simple composition and process to prepare matrix minitablets of mesalamine, within the size below 2.8 mm in any of its largest dimension, where the minitablets are able to swallow with soft foods or water.

Another object of the present disclosure is to provide a mesalamine matrix minitablets with high drug load percentage of 70% to 85% weight per weight (w/w) to the total weight of matrix minitablets administered by mixing with soft foods or water.

Another object of the present disclosure is to provide a composition to prepare matrix minitablets (beads) of mesalamine, where the matrix minitablets are able to release the mesalamine in controlled manner for prolonged period of time, equivalent to that of marketed product PENTASA® by similarity factor F2.

Another object of this disclosure is to provide matrix mesalamine product, free of reservoir type dosage forms or continuous controlled or delayed release characteristic functional coating to minitablets.

Another object of this disclosure is to provide matrix mesalamine product, which is optionally film coated for aesthetic appearance.

Another object of this disclosure is to administer the matrix mesalamine minitablets as multiunit dosage form either from encapsulated sachet or capsule by sprinkling/dispersing/suspending in soft food/water.

In another object of the present disclosure, dissolution profile of mesalamine matrix minitablets prepared with drug load percentage between 70% to 85% weight per weight (w/w) to the total drug loaded matrix minitablets, encapsulated in capsules is equivalent to the dissolution release profile of marketed product PENTASA® capsules in at least four pH's from pH 1.2, pH 4.5, pH 6.0, pH 6.5, pH 6.8, pH 7.2, and pH 7.5 by Model Independent Approach Using a Similarity Factor or difference factor. The test product yielding similarity factor of 50-100 with reference product is considered similar dissolution profile as that of reference.

SUMMARY OF THE INVENTION

In an aspect of the present disclosure, there is provided a pharmaceutical composition comprising: (a) mesalamine or its prodrug or derivatives thereof having a weight percentage in a range of 70-85 weight percentage with respect to the composition; (b) at least one controlled release excipient having a weight percentage in a range of 5-25 weight percentage with respect to the composition; (c) at least one binder having a weight percentage in a range of 2-6 weight percent with respect to the composition; and (d) at least one or mixture of diluents, glidants, lubricants and aesthetic agents having a weight percentage in a range of 1-25 weight percentage with respect to the composition.

These and other aspects of the embodiments herein will be better appreciated and understood when considered in conjunction with the following description. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

DETAILED DESCRIPTION OF INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

The term "mesalamine" used throughout the specification refers to not only mesalamine per se, but also its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof.

As used herein, the term "excipient" means any component admixed with or co-incorporated with the active agent. Excipients are safe for their intended use at the levels employed in the formulation and are compatible with the active agent. It is within the purview of the present invention to determine the type of excipient to be utilized in combination with the active agent as well as to determine how much excipient is to be added and the objective that the skilled artisan wishes to achieve by adding the same.

As used herein, the term "excipient" means any component admixed with or co-incorporated with the active agent. Excipients are safe for their intended use at the levels employed in the formulation and are compatible with the active agent. It is within the purview of the present disclosure to determine the type of excipient to be utilized in combination with the active agent as well as to determine how much excipient is to be added and the objective that the skilled artisan wishes to achieve by adding the same.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products, compositions, and methods are clearly within the scope of the disclosure, as described herein.

The embodiments herein and the various features and advantageous details thereof are explained more fully with reference to the non-limiting embodiments detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

In an embodiment of the present disclosure, there is provided a pharmaceutical composition comprising: (a) mesalamine or its prodrug or derivatives thereof having a weight percentage in a range of 70-85 weight percentage with respect to the composition; (b) at least one controlled release excipient having a weight percentage in a range of 5-25 weight percentage with respect to the composition; (c) at least one binder having a weight percentage in a range of 2-6 weight percent with respect to the composition; and (d) at least one or mixture of diluents, glidants, lubricants and aesthetic agents having a weight percentage in a range of 1-25 weight percentage with respect to the composition.

In an embodiment of the present disclosure, there is provided a pharmaceutical composition as described herein, wherein said pharmaceutical composition is in the form of matrix minitablets.

In an embodiment of the present disclosure, there is provided a pharmaceutical composition as described herein, wherein said pharmaceutical composition is granulated by either wet granulation or dry granulation or directly compressed.

In an embodiment of the present disclosure, there is provided a pharmaceutical composition as described herein, wherein said pharmaceutical composition is free of drug layering process, spheronization process, hot melt extrusion or melt granulation or functional coating, wherein said functional coating is a controlled release or delayed release characteristic polymeric coating.

In an embodiment of the present disclosure, there is provided a pharmaceutical composition as described herein, wherein said controlled release excipient is at least one selected from a group consisting of glyceryl dibehenate, stearic acid, ethyl cellulose and any solid lipid excipient; wherein said binders is at least one selected from a group consisting of polyvinyl pyrrolidine, ethyl cellulose, hydroxypropyl methyl cellulose (HPMC E5); and wherein at least one excipient extra granular excipients include at least one selected from ethyl cellulose, stearic acid, glyceryl dibehenate, magnesium stearate, talc, and colloidal silicon dioxide.

In an embodiment of the present disclosure, there is provided a pharmaceutical composition as described herein, wherein said monolithic matrix minitablets have largest dimension in the range of 1.00 mm to 2.8 mm.

In an embodiment of the present disclosure, there is provided a pharmaceutical composition as described herein, wherein said pharmaceutical composition is optionally coated with immediate release coating.

In an embodiment of the present disclosure, there is provided a pharmaceutical composition as described herein, wherein in said pharmaceutical composition the drug loading percentage is between 70-85%.

In an embodiment of the present disclosure, there is provided a pharmaceutical composition as described herein, wherein said pharmaceutical composition imparts an extended-release characteristic by releasing mesalamine NMT 30% at $1^{st}$ hour and NLT 75% at $6^{th}$ hour in pH 7.5; NMT 50% at $1^{st}$ hour and NLT 80% at $6^{th}$ hour in 0.1N HCL; and NMT 15% at $1^{st}$ hour and NLT 30% at $6^{th}$ hour in 4.5 pH in In vitro condition with USP II Apparatus and at 100 rpm.

In an embodiment of the present disclosure, there is provided a capsule encapsulating the pharmaceutical composition as described herein with drug load between 70-85% is equivalent to 250 mg or 500 mg of mesalamine.

In an embodiment of the present disclosure, there is provided a sachet encapsulating the pharmaceutical composition with drug load between 70-85% as described herein which is equivalent to 250 mg or 500 mg or 1 gm or 4 gm of mesalamine.

In an embodiment of the present disclosure, there is provided a capsule as described herein, wherein said capsule is opened and sprinkled in soft foods or water for oral administration.

In an embodiment of the present disclosure, there is provided a sachet as described herein, wherein said sachet is opened and sprinkled in soft foods or water for oral administration.

In an embodiment of the present disclosure, there is provided a composition of matrix minitablets (beads) for extended release of mesalamine without use of any controlled release or delayed release coating application, comprising a therapeutically effective amount of mesalamine, and a pharmaceutically acceptable excipient, wherein the pharmaceutically acceptable excipient is one at least selected from the group consisting of fillers/diluents, controlled release agents, binders, lubricant, glidants, aesthetic agents and mixtures thereof; and wherein the filler/diluent is optional and its selected from the group which includes, but are not limited, to at least one or a mixture of any of the excipients below, calcium phosphate and its derivatives, microcrystalline cellulose or pregelatinized starch, and wherein the pharmaceutically acceptable controlled release agent is selected from the group which includes, but are not limited, to at least one or a mixture of any of the excipient below glyceryl behenate/eicosadioate, glyceryl dibehenate, glyceryl distearate, glyceryl mono and dicaprylocaprate, glyceryl mono and dipalmitostearate, glyceryl monocaprylate, glyceryl monocaprylocaprate, glyceryl monostearate, glyceryl palmitostearate, glyceryl ricinoleate, glyceryl tristearate, polyoxyl glyceryl stearate, stearic acid, cetostearyl alcohol, sodium stearyl fumarate, stearyl alcohol, cetyl alcohol, diacetylated monoglycerides, medium chain triglycerides, stearoyl polyoxylglycerides, carnauba wax and yellow wax, and wherein the binder is selected from the group which includes, but are not limited, to at least one or a mixture of any of the excipients below polyvinylpyrrolidone (PVP), Ethyl cellulose (Viscosity <50 mPa·s), hydroxypropyl methyl cellulose (HPMC) (Viscosity <50 mPa·s) and its variants, hydroxypropyl cellulose (HPC) and its variants, starch and its derivatives, gelatin or any other known pharmaceutically acceptable binding agents, and wherein the "lubricant and glidant" used in herein refers to any substance that is added to improve flow and reduce friction during compression which includes, but are not limited, to at least one or a mixture of talc, magnesium silicate, magnesium stearate, sodium stearyl fumarate, colloidal silicon dioxide or the any controlled release agent used above therein found to have lubricant function, and wherein the other excipients used herein optionally to improve its color, flavor and finish aesthetics by using pharmaceutically acceptable coloring agent, flavoring agent and immediately soluble (non-functional) coating.

In an embodiment of the present disclosure, there is provided a process of preparation of matrix minitablets comprising of:
i) wet granulation, a) mesalamine alone or with at least one excipients like controlled release agent or diluent/filler are typically mixed b) granulated using wet binder prepared by dissolving binder in granulation solvent of either aqueous or organic nature c) the wet granules are wet sieved (optionally), dried (at temperature not more than 65° C.), d) screened through sieves, milled oversized retains till it pass through. e) screened granules are mixed with extra-granular excipients (if any), lubricants and glidants;
ii) dry granulation, a) mesalamine alone or with at least one excipient or mixture of excipients like controlled release agent, dry binder diluent/filler and optionally lubricant/glidant are typically mixed b) dry granulated by slugging and milling process, c) screened through sieves, milled oversized retains till it pass through. d) screened granules are mixed with extra-granular excipients (if any), lubricants and glidant;
iii) Direct Compression, a) mesalamine and at least one excipient of controlled release is mixed b) subsequently mixed "Mixture from a)" with other excipients like binder, diluent/filler, lubricant, glidant and other optional excipients.

In an embodiment of the present disclosure, the process further comprises compressing the mixture or granules obtained from i) wet granulation or ii) dry granulation or iii) direct compression in punch of size up to 2.8 mm as its largest dimension.

In an embodiment of the present disclosure, optional excipient like aesthetic agents (colorant and/or flavor) may be added either in granulating liquid or in lubrication stage before compression or otherwise by coating with immediate release or soluble film.

In an embodiment of the present disclosure, the mesalamine minitablets can be optionally cured at temperature of 40-50° C. for NMT 24 hours.

In an embodiment of the present disclosure, the minitablets can be encapsulated in capsules, wherein capsule is administered whole or only the contents by dispersing in water or by opening and spreading the minitablets in apple sauce or any soft foods.

In an embodiment of the present disclosure, the minitablets can be packed in sachets, wherein minitablets are to be administered by dispersing in water or by opening and spreading the minitablets in apple sauce or any soft foods.

In an embodiment of the present disclosure, the minitablets can be packed in multiple unit dose containers, wherein minitablets of respective unit dose prescribed are to be dispensed and taken either qualitatively (in a tablespoon or teaspoon) or quantitatively (in a volumetric device). The unit dose minitablets can be administered by dispersing in water or by opening and spreading the minitablets in apple sauce or any soft foods.

In an embodiment of the present disclosure, the minitablets can be utilized for rectal administration in a suitable vehicle.

In an embodiment of the present disclosure, the present disclosure concerns the process of preparation of mesalamine or its prodrugs/derivatives compositions which are capable of being compressed into matrix minitablets of extended-release characteristic without involvement of any controlled or delayed release polymeric coating process.

In an embodiment of the present disclosure, there is provided a composition and process to prepare matrix minitablets of mesalamine, with its largest dimension falls within the size range of 0.75 mm to 2.75 mm (i.e. below 2.8 mm), where minitablets can be swallowed with food, without urging to chew.

In an embodiment of the present disclosure, the simplest composition of matrix minitablets (beads) for extended release of mesalamine comprising a) mesalamine or its prodrug or derivatives thereof having a weight percentage in a range of 70-85 weight percentage with respect to the composition; b) at least one controlled release excipient having a weight percentage in a range of 5-25 weight percentage with respect to the composition; c) at least one binder having a weight percentage in a range of 2-6 weight percent with respect to the composition; and d) at least one or mixture of diluents, glidants, lubricants and aesthetic agents having a weight percentage in a range of 1-25 weight percentage with respect to the composition.

In an embodiment of the present disclosure, the simplest process for preparation of matrix minitablets (beads) for extended release of mesalamine comprising a) mesalamine or its prodrug or derivatives thereof having a weight percentage in a range of 70-85 weight percentage with respect to the composition; b) at least one controlled release excipient having a weight percentage in a range of 5-25 weight percentage with respect to the composition; c) at least one binder having a weight percentage in a range of 2-6 weight percent with respect to the composition; and d) at least one or mixture of diluents, glidants, lubricants and aesthetic agents having a weight percentage in a range of 1-25 weight percentage with respect to the composition; using wet granulation, dry granulation or direct compression.

In an embodiment of the present disclosure, the solvents used in wet granulation may be aqueous or non-aqueous.

In an embodiment of the present disclosure, the amount of diluent/filler may be optional and if it is added, percentage ranges from about 0.1 to 10 percent weight, in particular 5 to 10 percent weight based on the total weight of matrix minitablets composition.

In an embodiment of the present disclosure, the controlled release excipient or diluents is added partly intra-granular and partly extra-granular or completely in either intra-granular or extra-granular stages.

In an embodiment of the present disclosure, the amount of lubricant and glidant may vary within a range of about 1 to 15 percent weight based on the total weight of the matrix minitablets composition.

In an embodiment of the present disclosure, the amount of aesthetic agent (colorant, flavor or immediately soluble film coating) either alone or in combination may vary from about 0.05 to 5% w/w, preferably from 0.05 to 3 percent weight based on the total weight of matrix minitablets composition.

In an embodiment of the present disclosure, minitablets are free from functional controlled release coating polymers.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

EXAMPLES

The disclosure will now be illustrated with working examples, which is intended to illustrate the working of disclosure, not intended to take restrictively to imply any limitations on the scope of the present disclosure. Unless defined otherwise, all technical and scientific terms used herein have the same meaning as commonly understood to any one of the ordinary skilled in the art to which this disclosure belongs. Although methods and materials similar or equivalent to those described herein can be used in the practice of disclosed methods and compositions, the exemplary methods, devices and materials are described herein. It is to be understood that this disclosure is not limited to particular methods, and experimental conditions described, as such methods and conditions may apply.

Example 1: Formulations

The following formula (M1-M3) are examples of composition, wet granulation process and dissolution profile for preparing matrix minitablets.

TABLE 2a

| Ingredients | M1 (mg) | M2 (mg) | M3 (mg) |
|---|---|---|---|
| Mesalamine | 500 | 500 | 500 |
| Intragranular Excipients | | | |
| Glyceryl Dibehenate | 80 | 85 | 20 |
| Ethylcellulose | | | 20 |
| Binders | | | |
| Poly Vinyl Pyrrolidine (PVP K30) | 20 | 20 | |
| Ethyl cellulose (EC N7) | | | 20 |
| Binder vehicle (limited to acceptable levels in final product by drying) | | | |
| Water | q.s | q.s | |
| Ethanol | | | q.s |
| Extragranular Excipients | | | |
| Glyceryl Dibehenate | | 25 | 10 |
| Lubricants and Glidants | | | |
| Magnesium Stearate | | | 10 |
| Talc | | 10 | |
| Colloidal Silicon Dioxide | 5 | 5 | 5 |
| Aesthetic Agent | | | |
| Opadry II White | 15 | 15 | |
| Total (With Coating) | 656 | 635 | 575 |
| Size | 2.3 mm | 2.3 mm | 2 mm |
| Shape | Cylindrical | Cylindrical | Cylindrical |
| Core Minitablet Weight | 12.3 mg | 12.4 mg | 7.5 mg |

Process:

Step #1: Mesalamine is mixed with intragranular excipient

Step #2: Step #1 blend is loaded in High Shear Mixing Granulator and granulated using binder solution prepared using suitable vehicle.

Step #3: Wet granules (from Step #2) are dried at temperature NMT 65 C till the loss on drying (LOD) is below 2% or below 1% or as required using oven or fluidized bed dryer.

Step #4: Step #3 granules are milled and dry blended with extra granular excipients if any, then with lubricant and glidants.

Step #5: Final blend from step #4 is compressed in multitip round punches with respective diameter tip punches.

Step #6: Optionally coated with Opadry II white coating material

Step #7: Cured at 50 C for 4-12 Hours.

Step #8: Encapsulated in Size "00" capsules and performed dissolution.

TABLE 2b

Dissolution Results of Examples M1, M2 and M3 at different pH and its similarity factor against reference.

| | | Ph | | | | | | | |
|---|---|---|---|---|---|---|---|---|---|
| | | pH 1.2 | | pH 4.5 | | pH 6 | | pH 7.5 | |
| Formulation | Time (h) | R | T | R | T | R | T | R | T | Conclusion |
| M1 | 1 | 37 | 42 | 6 | 13 | 7 | 15 | 19 | 27 | Similarity factor |
| | 2 | 65 | 62 | 12 | 19 | 14 | 23 | 38 | 43 | (f2) metric is met |
| | 4 | 89 | 81 | 22 | 31 | 27 | 37 | 67 | 65 | in all the four-pH |
| | 6 | 93 | 91 | 30 | 40 | 39 | 50 | 85 | 77 | on comparing |
| | 8 | 100 | 97 | 37 | 47 | 49 | 59 | 94 | 88 | with reference |
| | 12 | | | 51 | 60 | 65 | 72 | 101 | 94 | |
| | f2 | 66 | | 62 | | 52 | | 60 | | |

TABLE 2b-continued

Dissolution Results of Examples M1, M2 and M3 at different pH and its similarity factor against reference.

| Formulation | Time (h) | pH 1.2 R | pH 1.2 T | pH 4.5 R | pH 4.5 T | pH 6 R | pH 6 T | pH 7.5 R | pH 7.5 T | Conclusion |
|---|---|---|---|---|---|---|---|---|---|---|
| M2 | 1 | 37 | 37 | 6 | 10 | 7 | 13 | 19 | 26 | Similarity factor |
|  | 2 | 65 | 57 | 12 | 17 | 14 | 21 | 38 | 40 | (f2) metric is met |
|  | 4 | 89 | 81 | 22 | 28 | 27 | 32 | 67 | 63 | in all the four-pH |
|  | 6 | 93 | 93 | 30 | 38 | 39 | 44 | 85 | 77 | on comparing |
|  | 8 | 100 | 100 | 37 | 44 | 49 | 55 | 94 | 85 | with reference |
|  | 12 |  |  | 51 | 58 | 65 | 70 | 101 | 95 |  |
|  | f2 |  | 64 |  | 60 |  | 62 |  | 59 |  |
| M3 | 1 | 37 | 45 | 6 | 15 | 7 | 18 | 19 | 30 | Similarity factor |
|  | 2 | 65 | 61 | 12 | 21 | 14 | 27 | 38 | 43 | (f2) metric is met |
|  | 4 | 89 | 82 | 22 | 30 | 27 | 37 | 67 | 60 | in all the four-pH |
|  | 6 | 93 | 95 | 30 | 35 | 39 | 47 | 85 | 70 | on comparing |
|  | 8 | 100 | 101 | 37 | 44 | 49 | 53 | 94 | 88 | with reference |
|  | 12 |  |  | 51 | 54 | 65 | 62 | 101 | 92 |  |
|  | f2 |  | 63 |  | 51 |  | 52 |  | 51 |  |

The f2 metric above 50 in different buffers of trials M1 M2 and M3 indicates that the matrix minitablets prepared by the selected composition and simplified process without involving any melting, inglobation, spheronization, pareil seeds, drug or controlled release polymeric layering or coating.

The following formula (M4-M6) are examples of composition, wet granulation process at high temperature (i.e. melting) and sintered minitablets dissolution profile.

TABLE 3A

| Ingredients | M4 (mg) | M5 (mg) | M6 (mg) |
|---|---|---|---|
| Mesalamine | 500 | 500 | 500 |
| Intragranular Excipients |  |  |  |
| Glyceryl Dibehenate | 160 | 70 |  |
| Stearic Acid |  |  | 50 |
| Binders |  |  |  |
| Poly Vinyl Pyrrolidine (PVP K30) | 20 | 20 | 40 |
| Binder vehicle (limited to acceptable levels in final product by drying) |  |  |  |
| Water | q.s | q.s | q.s |
| Extragranular Excipients |  |  |  |
| Glyceryl Dibehenate | 20 | 20 |  |
| Stearic Acid |  |  | 12 |
| Lubricants and Glidants |  |  |  |
| Magnesium Stearate | 7 | 13.5 |  |
| Colloidal Silicon Dioxide | 5 | 6.5 | 6 |

TABLE 3A-continued

| Ingredients | M4 (mg) | M5 (mg) | M6 (mg) |
|---|---|---|---|
| Aesthetic Agent |  |  |  |
| Opadry II White |  | 15 | 15 |
| Total (With Coating) | 712 | 645 | 623 |
| Size | 1.5 mm | 2 mm | 2.5 mm |
| Shape | Cylindrical | Cylindrical | Cylindrical |
| Core Minitablet Weight | 3.2 mg | 7.5 mg | 15 mg |

Process:

Step #1: Mesalamine is mixed with intragranular excipient

Step #2: Step #1 blend is loaded in High Shear Mixing Granulator and granulated using binder solution prepared using suitable vehicle.

Step #3: M4—Wet granules (from Step #2) are dried (sintered) at temperature of 80 C till the loss on drying (LOD) is below 2% or below 1% or as required using oven or fluidized bed dryer to inglobate the active in controlled release agent.

M5 & M6—Wet granules (from Step #2) are dried at temperature NMT 65 C till the loss on drying (LOD) is below 2% or below 1% or as required using oven or fluidized bed dryer.

Step #4: Step #3 granules are milled and dry blended with extra granular excipients, then with lubricant and glidants.

Step #5: Final blend from step #4 is compressed in multitip round punches with respective diameter tip punches.

Step #6: Optionally coated with Opadry II white coating material

Step #7: M4—Cured at 50 C for 4-12 Hours.

M5—Sintered at 80 C for 30 mins

M6—Sintered at 80 C for 30 mins

Step #8: Encapsulated in Size "00" capsules.

TABLE 3b

Dissolution Results of Examples M1, M2 and M3 at different pH and its similarity factor against reference.

| Formulation | Time (h) | pH 1.2 | | pH 4.5 | | pH 6 | | pH 7.5 | | Conclusion |
|---|---|---|---|---|---|---|---|---|---|---|
| | | R | T | R | T | R | T | R | T | |
| M4 | 1 | 37 | 44 | 6 | 17 | 7 | 19 | 19 | 29 | Similarity factor |
| | 2 | 65 | 58 | 12 | 23 | 14 | 28 | 38 | 44 | (f2) metric is |
| | 4 | 89 | 81 | 22 | 36 | 27 | 42 | 67 | 61 | failed to meet in |
| | 6 | 93 | 89 | 30 | 45 | 39 | 52 | 85 | 72 | three buffers on |
| | 8 | 100 | 96 | 37 | 52 | 49 | 59 | 94 | 79 | comparing with |
| | 12 | | | 51 | 64 | 65 | 66 | 101 | 84 | reference |
| | f2 | 59 | | 44 | | 46 | | 46 | | |
| M5 | 1 | 37 | 42 | 6 | 12 | 7 | 13 | 19 | 26 | Similarity factor |
| | 2 | 65 | 83 | 12 | 21 | 14 | 21 | 38 | 38 | (f2) metric is |
| | 4 | 89 | 95 | 22 | 34 | 27 | 41 | 67 | 62 | failed to meet in |
| | 6 | 93 | 100 | 30 | 46 | 39 | 53 | 85 | 75 | three buffers on |
| | 8 | 100 | | 37 | 56 | 49 | 63 | 94 | 81 | comparing with |
| | 12 | | | 51 | 68 | 65 | 71 | 101 | 88 | reference |
| | f2 | 49 | | 43 | | 48 | | 52 | | |
| M6 | 1 | 37 | 40 | 6 | 16 | 7 | 16 | 19 | 24 | Similarity factor |
| | 2 | 65 | 59 | 12 | 24 | 14 | 22 | 38 | 34 | (f2) metric is |
| | 4 | 89 | 79 | 22 | 34 | 27 | 33 | 67 | 48 | failed to meet in |
| | 6 | 93 | 90 | 30 | 41 | 39 | 43 | 85 | 60 | two buffers on |
| | 8 | 100 | 97 | 37 | 48 | 49 | 49 | 94 | 71 | comparing with |
| | 12 | | | 51 | 63 | 65 | 65 | 101 | 78 | reference |
| | f2 | 61 | | 47 | | 62 | | 36 | | |

Advantages of the Present Disclosure

Existing technologies used in preparing extended release minitablets of mesalamine or its prodrugs or derivatives thereof firstly involve preparation of a) granulated mesalamine or b) mesalamine layered sugar spheres/non pareil seeds or c) pellets by hot melt extrusion or d) melt granulation. They are further coated with polymer of delayed, controlled or extended-release characteristic. These processes are established to be involving multiple steps, more energy and time consuming. Also, the drug layering on sugar spheres or any inert non-pareil seeds involves the use of large volume of organic solvents, and necessitates multiple steps, thereby making the whole process more expensive and time consuming. Further, the extrusion and spheronization involves multiple steps, multiple control parameters, more energy (particularly heating and cooling process) and is time consuming. To overcome the above drawbacks the present disclosure discloses pharmaceutical composition for simplified processing of mesalamine or its prodrugs/derivatives as minitablets such that the largest dimension of the minitablet is less than 2.8 mm, circumventing the need for use of any coating polymers to impart extended-release characteristic similar to that of PENTASA. The composition of the present disclosure is devoid of non-pareil seeds, and the processes adopted to prepare the composition are free of melting technique or extrusion and spheronization technique.

We claim:
1. A pharmaceutical composition comprising:
   (a) mesalamine or its prodrug or derivatives thereof having a weight percentage in a range of 70-85 weight percentage with respect to the composition;
   (b) a controlled release excipient having a weight percentage in a range of 5-25 weight percentage with respect to the composition, wherein the controlled release excipient is glyceryl dibehenate;
   (c) at least one binder having a weight percentage in a range of 2-6 weight percent with respect to the composition; and
   (d) at least one or mixture of diluents, glidants, lubricants and aesthetic agents having a weight percentage in a range of 1-25 weight percentage with respect to the composition;
   wherein said pharmaceutical composition is free of drug layering process, acidic or basifying agents, spheronization process, hot melt extrusion or melt granulation or reservoir, functionally coated matrix, wherein said functional coating is a controlled release or delayed release characteristic polymeric coating.

2. The pharmaceutical composition as claimed in claim 1, wherein said pharmaceutical composition is in the form of matrix minitablets.

3. The pharmaceutical composition as claimed in claim 1, wherein said pharmaceutical composition is granulated by either wet granulation or dry granulation or directly compressed.

4. The pharmaceutical composition as claimed in claim 1, wherein said binders is at least one selected from a group consisting of polyvinyl pyrrolidine, ethyl cellulose, hydroxypropyl methyl cellulose (HPMC); and wherein at least one or mixture of diluents, glidants, lubricants and aesthetic agents is at least one selected from ethyl cellulose or other cellulose derivatives, stearic acid or inorganic stearic acid derivatives, glyceryl dibehenate, PVA, HPMC, magnesium stearate, talc, and colloidal silicon dioxide.

5. The pharmaceutical composition as claimed in claim 1, wherein said matrix minitablets have largest dimension in the range of 1.00 mm to 2.8 mm.

6. The pharmaceutical composition as claimed in claim 1, wherein said pharmaceutical composition is optionally coated with immediate release coating.

7. The pharmaceutical composition as claimed in any one of claims 1-3 and 4-6, wherein said pharmaceutical composition imparts an extended-release characteristic by releasing mesalamine NMT 30% at 1S hour and NLT 75% at 6 tl hour in pH 7.5; NMT 50% at 1" hour and NLT 80% at 6 tl hour in 0.1N HCL; and NMT 15% at 1S hour and NLT 30% at 6 tl hour in 4.5 pH in In vitro condition with USP II Apparatus and at 100 rpm.

8. A capsule encapsulating the pharmaceutical composition as in any of claim 7 with drug load between 70-85% is equivalent to 250 mg or 500 mg of mesalamine.

9. A sachet encapsulating the pharmaceutical composition with drug load between 70-85% as in any of claim 7 is equivalent to 250 mg or 500 mg or 1 gm or 4 gm of mesalamine.

10. A capsule as claimed in claim 8, wherein said capsule is opened and sprinkled in soft foods or water for oral administration.

11. A sachet as claimed in claim 9, wherein said sachet is opened and sprinkled in soft foods or water for oral administration.

\* \* \* \* \*